(12) United States Patent
Baird, Jr. et al.

(10) Patent No.: US 6,589,416 B2
(45) Date of Patent: *Jul. 8, 2003

(54) METHOD AND CATALYST FOR OPENING NAPHTHENIC RINGS OF NAPHTHENIC RING-CONTAINING COMPOUNDS

(75) Inventors: William C. Baird, Jr., Baton Rouge, LA (US); Darryl P. Klein, Ellicott City, MD (US); Michele S. Touvelle, Baton Rouge, LA (US); Jingguang G. Chen, Hockessin, DE (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/897,301

(22) Filed: Jul. 2, 2001

(65) Prior Publication Data

US 2002/0050466 A1 May 2, 2002

Related U.S. Application Data

(60) Provisional application No. 60/219,970, filed on Jul. 21, 2000.

(51) Int. Cl.$^7$ .................. C10G 35/085; C07C 5/00; B01J 23/40; B01J 23/42; B01J 23/46
(52) U.S. Cl. .................. 208/138; 208/133; 208/134; 208/137; 208/15; 585/700; 585/940; 502/325; 502/326; 502/327
(58) Field of Search ............... 585/700, 940; 208/133, 134, 137, 138, 15; 502/326, 327, 325

(56) References Cited

U.S. PATENT DOCUMENTS

| | | | |
|---|---|---|---|
| 3,617,485 A | 11/1971 | Kittrell ................. 208/59 |
| 3,617,511 A | 11/1971 | Jenkins et al. .......... 208/112 |
| 3,631,117 A | 12/1971 | Kovach et al. .......... 260/666 |
| 3,779,897 A | 12/1973 | Wrench et al. .......... 208/89 |
| 3,943,052 A | 3/1976 | Kmak et al. ............ 208/140 |
| 3,953,368 A | 4/1976 | Sinfelt ................. 252/466 |
| 4,018,670 A | 4/1977 | Sinfelt et al. .......... 208/140 |
| 4,046,673 A | 9/1977 | Paynter et al. .......... 208/140 |
| 4,134,823 A | 1/1979 | Bertolacini et al. ...... 208/65 |
| 4,140,626 A | 2/1979 | Bertolacini et al. ...... 208/216 |
| 4,224,192 A | 9/1980 | Foster et al. .......... 252/466 B |
| 4,783,575 A | 11/1988 | Schmidt et al. .......... 585/748 |
| 4,834,866 A | 5/1989 | Schmidt ................. 208/65 |
| 4,956,075 A | 9/1990 | Angevine et al. ......... 208/120 |
| 5,015,614 A | 5/1991 | Baird, Jr. et al. ....... 502/250 |
| 5,026,950 A | 6/1991 | Schmidt et al. .......... 585/737 |
| 5,334,792 A | 8/1994 | Del Rossi et al. ........ 585/314 |
| 5,345,026 A | 9/1994 | Chang et al. ............ 585/700 |
| 5,463,155 A | 10/1995 | Galperin et al. ......... 585/310 |
| 5,763,731 A | 6/1998 | McVicker et al. ......... 585/737 |
| 5,770,042 A | 6/1998 | Galperin et al. ......... 208/65 |
| 5,811,624 A | 9/1998 | Hantzer et al. .......... 585/700 |
| 5,888,922 A | 3/1999 | Galperin ................ 502/163 |
| 5,906,728 A | 5/1999 | Iaccino et al. .......... 208/61 |
| 5,925,239 A | 7/1999 | Klein et al. ............ 208/213 |
| 5,928,498 A | 7/1999 | McVicker et al. ......... 208/213 |
| 5,935,420 A | 8/1999 | Baird, Jr. et al. ....... 208/213 |
| 5,993,642 A | 11/1999 | Mohr et al. ............. 208/46 |
| 6,221,240 B1 | 4/2001 | Klein et al. ............ 208/213 |

OTHER PUBLICATIONS

Schultz and co–workers (Proc. 5th Intl. Catal. Congr., North–Holland Publ. (Aidam), v.2, 1229–39, (1973)), no month.
Egan, et al., J. Amer. Chem. Soc., 84, 1204–12 (1962), no month.
Gault, et al., Adv. Catal., 30, 1–95, (1981), no month.
Weitkamp, et al., in Structure and Reactivity of Modified Zeolites, Elsevier (Adam), 279–90, (1984)), no month.
Sergienko, et al., Khim. Geol. Nauk., 2, 65–70 (1976), no month.

*Primary Examiner*—Nadine G. Norton
(74) *Attorney, Agent, or Firm*—Gerard J. Hughes; Jeremy J. Kliebert

(57) ABSTRACT

Disclosed is a process for opening naphthenic rings of naphthenic ring-containing compounds, and catalysts which can be used in that process. The naphthene ring opening catalyst is a polymetallic catalyst comprising Group VIII metals. In a preferred embodiment the naphthene ring opening catalyst comprises Ir in combination with a Group VIII metal selected from at least one of Pt, Rh, and Ru, in an amount effective for opening a naphthene ring-containing compound at a tertiary carbon site.

16 Claims, No Drawings

METHOD AND CATALYST FOR OPENING NAPHTHENIC RINGS OF NAPHTHENIC RING-CONTAINING COMPOUNDS

CROSS REFERENCE TO RELATED APPLICATION

This case claims benefit of U.S. Provisional Patent Application No. 60/219,970 filed Jul. 21, 2000.

FIELD OF THE INVENTION

This invention relates to a method and composition for opening naphthenic rings of naphthenic ring-containing compounds such as distillate. In particular, this invention relates to the use of a catalyst composition comprising Ir in combination with at least one of Pt, Ru, and Rh.

BACKGROUND OF THE INVENTION

There is an increasing demand for hydrocarbons boiling in the distillate boiling point range ("distillate"). Distillates typically contain paraffins, naphthenes, and aromatics. For fuel quality parameters such as cetane number, gravity and emissions, paraffins are the most desirable components, followed by naphthenes, followed by aromatics. The least desirable are multi-ring aromatic compounds. There is also an increasing demand for paraffinic solvents arising from their low toxicity and biodegradability. Consequently, it is desirable to reduce the cyclic compound content of hydrocarbon solvent blends, in general, and to convert naphthenes to paraffins, in particular. The general process of converting naphthenes to paraffins is referred to herein as ring opening.

Refinery processes that produce distillate fuels often have a limited capability to produce high quality and yields of distillate fuel. For example, conventional hydrogenation processes saturate aromatic rings to form naphthenes, thereby increasing the cetane number and increasing the API gravity (i.e., lowering the density). However, single ring and multi-ring naphthenes have generally lower cetane values and are denser than paraffins having substantially the same number of carbon atoms. The greater density of naphthenes results in reduced volume of the distillate fuel blend relative to compositions containing similar concentrations of paraffins instead of naphthenes. Hydrocracking catalysts, typically composed of hydrogenation metals supported on acidic supports, are also effective for aromatics hydrogenation and for ring opening by cracking. However, cracking tends to make lower boiling point products, including a significant quantity of undesired gas by-products, which lowers the overall boiling range and limits the volume of final distillate product. In fact, hydrocracking products generally do not contain more distillate boiling range paraffins than the hydrocracking feeds. Moreover, a significant portion of the total paraffin concentration in the final product of conventional hydrocracking processes, including gas by-products, are relatively low molecular weight compounds that are outside the distillate boiling range. Thus, the apparent increase in distillate boiling range paraffins and improved distillate fuel quality may result primarily from a combination of the hydrogenation of aromatics and a concentration of paraffins in a reduced volume of distillate product, the latter arising from removing the undesired paraffin gas by-product, i.e., the low boiling point paraffin gas components.

There is, therefore, a need for selective ring opening processes for converting single and multi-ring aromatic species, including alkyl functionalized derivatives thereof, into distillate boiling range paraffins without producing a significant amount of undesirable low boiling point saturated species. Selectivity for ring opening is related to the propensity for cleavage of a ring bond which results in product molecules having an equivalent number of carbon atoms and at least one less ring than the original molecule, rather than cleavage of a bond which results in a product molecule having fewer carbons than the original molecule. A perfectly selective ring opening process would give only ring bond cleavage to produce molecules having an equivalent number of carbon atoms and at least one less ring than the original molecule. For example, from a hydrocarbon stream containing only single ring naphthenes of n number of carbon atoms, the product from perfect ring opening selectivity would contain only paraffins of n number of carbon atoms. Thus, the greater number of product molecules from a ring opening process having an equivalent number of carbon atoms and at least one less ring than the original molecule, the greater the selectivity for ring opening.

Conventional ring opening processes use a wide range of catalysts, including bifunctional metal hydrogenation-acidic catalysts. Distillate quality may be improved by controlling paring isomerizations and subsequent dealkylations in order to limit the number of lower cetane, highly branched paraffins that may result from conventional ring opening.

Some conventional processes for forming an improved distillate employ Ir catalysts for opening naphthene ring compounds. Even though distillates such as diesel, jet fuel, and heating oil contain at least about 20 vol. %, generally about 20 to about 40 vol. % of $C_6$ naphthenes, the conventional processes open $C_6$ naphthenes at low rates, if at all. This problem is exacerbated with hydrotreated distillates because they have a still greater concentration of $C_6$ naphthenes. In order to overcome this problem of poor opening of $C_6$ naphthene rings, U.S. Pat. No. 5,763,731 teaches using Ir along with at least one acidic co-catalyst, preferably a zeolite, to isomerize the $C_6$ naphthene rings to $C_5$ rings. However, since the resulting $C_5$ ring structure will typically bear increased numbers of substituents, such as alkyl groups, this approach increases the volume of branched paraffins upon ring opening. In addition, the presence of an acidic co-catalyst has a tendency to isomerize any naturally present linear paraffin into a branched paraffin, often resulting in a ring-opened product that has an undesirably high concentration of branched paraffins. Moreover, the process results in increased light saturated gas production, particularly at high temperature.

Another conventional process, set forth in U.S. Pat. No. 5,811,624, uses Ir along with at least certain transition metals for isomerizing $C_6$ naphthene rings to $C_5$ naphthene rings, with the Ir component being particularly effective for opening the $C_5$ naphthene rings. However, the product contains a significant concentration of branched paraffins, which leads to a lower product cetane number. There is still a need, therefore, for a ring opening process and catalyst which provide a much higher degree of linear paraffin functionality in the ring opened product, and at the same time, provide a greater volume of product in the distillate range.

SUMMARY OF THE INVENTION

A ring opening catalyst and process are provided to form a reduced number of ring structures in the product stream, minimize dealkylation of any pendant substituents optionally present on the ring structure, and increase volume of the product. In particular, the invention is beneficial in that it provides a relatively high content of more linear paraffins in the product. In one embodiment, the invention provides paraffins having a more linear (i.e., less branchy) character than conventional methods and catalysts using feeds containing both $C_5$ and $C_6$ naphthene ring compositions having tertiary carbons. The ring-opened product provides a diesel or jet fuel product, which has a high degree of linear and less branched paraffins, particularly one having a high degree of linear and less branched $C_9^+$ paraffins. This translates to a fuel product which is high in cetane number, a highly sought after-fuel quality.

Specifically, a catalyst is provided which is highly selective in converting naphthene feed into paraffin product containing a substantial quantity of linear and less branched paraffins. The invention is particularly beneficial in converting naphthene feed containing a $C_6$ naphthene ring-containing composition, wherein the $C_6$ ring contains at least one tertiary carbon, to a product containing a substantial quantity of linear and less branched paraffin compounds.

In one embodiment there is provided a polymetallic Group VIII naphthene ring opening catalyst. The naphthene ring opening catalyst preferably comprises Ir in combination with at least one other Group VIII metal selected from Pt, Ru, and Rh, in an amount effective for opening a naphthene ring-containing compound at a tertiary carbon site. In a preferred embodiment, the other Group VIII metal is Pt. The ring opening catalyst may be supported on a refractory inorganic oxide selected from the group consisting of alumina, silica, zirconia, titania, chromia, zinc oxide, magnesia, thoria, boria, silica-alumina, silica-magnesia, chromia-alumina, alumina-boria, silica-zirconia, and combinations thereof The Ir and the other, or "second", Group VIII metal are present in an amount effective for opening a naphthene ring at a tertiary carbon site. Desirably, Ir is present in a range of about 0.1 to about 2.0 wt. %, preferably in a range of about 0.3 to about 1.5 wt. %, more preferably in a range of about 0.5 to about 1.2 wt. %, and most preferably in a range of about 0. to about 1.0 wt. %, based on the weight of the ring opening catalyst. It is also desirable that the second Group VIII metal be present in a range of about 0.001 to about 2.0 wt. %, preferably in a range of about 0.005 to about 1.5 wt. %, more preferably in a range of about 0.007 to about 1.3 wt. %, and most preferably in a range of about 0.01 to about 1.0 wt. %, based on the weight of the ring opening catalyst.

In another embodiment, there is provided a process for opening naphthene rings of naphthene ring-containing compounds in a feed stream. The process comprises providing a naphthene ring-containing feed stream; and contacting the naphthene ring-containing feed stream with a catalyst comprising Ir in combination with a second Group VIII metal selected from Pt, Rh, Ru, and combinations thereof in an amount effective for opening a naphthene ring-containing compound at a tertiary carbon site under effective ring opening conditions.

In a preferred embodiment, the ring opening process further comprises ring opening naphthene rings having at least one tertiary carbon site at the tertiary carbon site, thereby forming a ring opened product having increased linear paraffin functionality relative to that of the feed stream. The process may also include recovering the ring-opened product. The ring opened product may be used directly, for example, as a diesel fuel, jet fuel, gas oil, and heating oil, and it may also be blended with other petroleum streams for use as a diesel fuel, jet fuel, gas oil, and heating oil. Preferably, the ring opened product is blended with a petroleum stream having a boiling point ranging from about 175° C. to about 600° C., wherein the blend has a cetane number of at least about 40.

Ring opening may be carried out at a temperature ranging from about 150° C. to about 400° C.; a total pressure ranging from about 100 to about 3,000 psig, a liquid hourly space velocity ranging from about 0.1 to about 10 V/V/Hr, and a hydrogen treat gas rate ranging from about 200 to about 10,000 standard cubic feet per barrel (SCF/B). The feed stream in the ring opening process is preferably a petroleum feed stream which has a boiling point of from about 175° C. to about 600° C., more preferably about 175° C. to about 500° C.

Preferably, the preferred ring opening catalysts are capable of ring opening at least about 20% of an amount of 1,2-dimethylcyclohexane at the tertiary carbon site. More preferably, the ring opening catalysts are capable of ring opening between about 30% and about 40% of the amount of 1,2-dimethylcyclohexane at the tertiary carbon site.

The invention further relates to a product made by the ring opening process. The product is higher in linear paraffin functionality compared to conventional ring opened products.

DETAILED DESCRIPTION OF THE INVENTION

The invention is based in part on the discovery of ring opening catalyst compositions useful in processes for forming high cetane number distillate having a desirable concentration of compounds, which have a high degree of linear paraffin functionality. More particularly, the catalyst compositions are useful for opening rings at tertiary carbon sites in naphthene or naphthenic ring-containing distillates in order to form products with a high degree of linear paraffin functionality. The compositions are especially effective in opening compounds containing $C_5$ and $C_6$ naphthene rings bearing at least one tertiary carbon.

As defined herein, compounds having a high degree of linear paraffin functionality have fewer paraffin (i.e., alkyl) side chains and longer paraffin substituents. According to this definition, linear paraffins, particularly $C_{10}$–$C_{20}$ linear paraffins, are the most highly desirable compounds for use as a diesel or jet fuel product, though other compounds having a relatively high degree of linear paraffin functionality are also acceptable. For example, a cycloalkane ring compound having a single, linear alkyl side chain has relatively high paraffin functionality compared to a cycloalkane ring having multiple side chains. By the same definition, an aromatic ring compound having a single, linear alkyl side chain has a relatively high linear paraffin functionality compared to an aromatic ring compound having multiple side chains.

As defined herein, a tertiary carbon (3° carbon) is the site of location of a substituent group on a naphthenic ring compound. Tertiary carbons are represented by such structural features, for example, as —CH(R)—CH$_2$— and —CH(R)—CH(R)— where R is a carbon-containing chain, preferably a $C_1$–$C_{10}$ carbon-containing chain.

Opening the ring structure of naphthenic ring compounds at the tertiary carbon site, known as tertiary bond cleavage, is particularly desirable for $C_6$ naphthenic rings. Tertiary bond cleavage is advantageous because isomerization of the $C_6$ rings to $C_5$ rings is abated so that the ring-opened product will have a high degree of linear paraffin functionality.

As used herein, a naphthene or a naphthenic ring-containing composition refers to a cycloalkane or a composition containing at least one cycloalkane ring in its structure. For example, the term can refer to either a $C_5$ or $C_6$ ring-membered cycloparaffin. The cycloparaffin can also include various side chains, particularly one or more alkyl side chains of 1–10 carbons. In addition, the cycloparaffin can be attached or fused to other ring structures, forming two or three membered ring compounds. The additional ring members can be saturated or unsaturated, as long as at least one ring of the complete structure contains a tertiary carbon. Examples of two and three membered ring structures that can contain a tertiary carbon include saturated or partially saturated naphthalenes, indenes, fluorenes, phenanthrenes, anthracenes, acenaphthalenes, and biphenylenes.

A feedstream which is to be ring opened will typically contain a mix of hydrocarbons having one or more of the naphthene ring-containing compositions, and the naphthene ring-containing compositions preferably contain at least one alkyl substituent. Preferably, the feedstream will comprise at least 5 vol. % of at least one naphthenic ring-containing compound more preferably at least 25 wt. %, most preferably at least 50 wt. %. Typically the feedstream will comprise from about 5 to about 85 vol. % of at least one naphthenic ring-containing compound, based on the volume of the feedstream.

In a more preferred embodiment, the hydrocarbon containing the naphthene ring compositions that are to be opened will include $C_5$ and $C_6$ naphthene ring compounds that do not include additional ring members. Non-limiting examples of these compounds include methylcyclopentanes, ethylcyclopentanes, propylcyclopentanes, butylcyclopentanes, pentylcyclopentanes, methylcyclohexanes, ethylcyclohexanes, propylcyclohexanes, butylcyclohexanes, and pentylcyclohexanes. Preferably, the $C_5$ and $C_6$ ring naphthene ring compounds contain alkyl substituents.

Naphthenic ring-containing compounds are found in a wide variety of hydrocarbon feeds, such as petroleum streams boiling in the distillate range. These streams will typically include a variety of chemical compounds, including multi-ring compositions. Preferably, this invention uses a petroleum feed stream having a boiling point ranging from about 175° C. to about 600° C. Examples of such a feed stream include diesel fuel, jet fuel, heating oil, gas oil, and light cycle oil. Gas oil includes vacuum gas oil boiling in the range of from about 340° C. to about 565° C., which is typically derived from vacuum distillation of crude oil, or it can be obtained by conversion of products such as coker gas oil or heavy cat cycle oil. Other feed streams can also be used if appropriately pre-treated. These streams include chemical feed streams and lube streams.

The preferred naphthene ring opening catalysts are polymetallic Group VIII noble metal catalysts. Preferred as the polymetallic Group VIII noble metal catalysts of this invention are catalysts, which comprise Ir in combination with Pt, Rh, and Ru, or mixtures thereof Preferred polymetallic Group VIII noble metal catalysts are Pt—Ir, Rh—Ir, and Ru—Ir. Pt—Ir and Rh—Ir are more preferred, and Pt—Ir is most preferred. The Ir content of these catalysts may range from about 0.1 to about 2 wt. %, preferably about 0.3 to about 1.5 wt. %, more preferably about 0.5 to about 1.2 wt. %, and most preferably about 0.5 to about 1.0 wt. %. The content of the second Group VIII metal in a bimetallic composition may range from about 0.001 to about 2.0 wt. %, preferably about 0.005 to about 1.5 wt. %, more preferably about 0.007 to about 1.3 wt. %, and most preferably about 0.01 to about 1 wt. %. Preferred catalyst compositions (wt. %) include 0.01Me-0.9Ir, 0.05Me-0.9Ir, 0.1Me-0.9Ir, 0.3Me-0.9Ir, and 0.6Me-0.9Ir where Me is at least one of Pt, Rh, and Ru.

The naphthene ring opening catalysts may be supported on a substrate material. Preferred support materials include refractory inorganic oxide selected from the group of alumina, silica, zirconia, titania, chromia, zinc oxide, magnesia, thoria, boria, silica-alumina, silica-magnesia, chromia-alumina, alumina-boria, silica-zirconia, and combinations thereof. Alumina supports are particularly preferred. Supports having an essential absence of acid character, such as alumina, are preferred.

The naphthene ring opening catalysts may be prepared by conventional techniques utilizing incipient wetness or the absorption of the metal precursors from excess aqueous solution. Suitable metal precursors are the halides, the halometallic acids, nitrates, nitrites, amine halo complexes, amine nitrate complexes, and amine nitrite complexes. Metals deposition from organic solvents may also be practiced using organometallic complexes such acetylacetonates, carbonyls and the like. Decomposition of the deposited complexes may be accomplished thermally in an air, hydrogen, or inert atmosphere by conventional heating, or by the application of microwave or ultrasonic radiation. The naphthene ring opening catalysts may or may not contain Cl depending on the method of synthesis.

The naphthene ring opening catalysts can be activated according to conventional methods. For example, they may be activated by drying in air at a temperature ranging from about ambient temperature to about 300° C. for about 4 to about 24 hours and reducing in-flowing hydrogen, preferably in situ, at a temperature ranging from about 200° C. to about 600° C. for about 0.5 to about 24 hours. Drying at temperatures below 200° C. and reducing at about 350° C. to about 500° C. for about 4 hours are preferred.

As discussed, the preferred ring opening catalyst compositions are useful in processes for forming high cetane number distillate having a desirable concentration of compounds which have a high degree of linear paraffin functionality. To convert naphthene compounds to paraffins, a catalytically effective amount of at least one catalyst of this invention is contacted with an appropriate feed stream under catalytic ring opening conditions. Preferred conditions are such that the $C_5$ and $C_6$ rings of the naphthene compounds are opened when contacted with the catalyst. While conventional process conditions may be employed, preferred process conditions include a temperature from about 150° C. to about 400° C., preferably from about 225° C. to about 350° C., a total pressure ranging from about 100 to about 3,000 psig, preferably from about 100 to about 2,200 psig, more preferably about 100 to about 1,500 psig, a liquid hourly space velocity ranging from about 0.1 to about 10, preferably from about 0.5 to about 5 V/V/Hr; and a hydrogen treat gas rate of about 200 to about 10,000 SCF/B, preferably about 500 to about 5000 SCF/B. SCF/B means standard cubic feet per barrel, and V/V/Hr means volume of feed per volume of catalyst per hour.

Conventional ring opening reactors may be used in the ring opening process of this invention. A fixed bed reactor system wherein the feedstock is passed over one or more stationary beds of catalyst is preferred. Multiple reactors may be used in either series or parallel configurations.

Hydrogen gas (i.e., a hydrogen-containing treat gas) conducted to the reaction process may flow over the catalyst either in a direction co-current or countercurrent with the feedstock. Hydrogen is supplied to saturate the carbons where ring opening occurs, and it is preferably supplied in stoichiometric excess. In one embodiment, the reactor effluent is passed to a separation zone where hydrogen that has not been consumed in the reaction process is separated and suitably recycled to the reaction zone together with make-up hydrogen as needed. In another embodiment, the treat gas is employed in a "once-through" arrangement and is therefore not recycled.

Countercurrent reactors incorporating the preferred catalyst are a preferred embodiment since properly constructed countercurrent reactors can provide better contacting of reactants and treat gas. They are particularly beneficial in maintaining a low $H_2S$ partial pressure. Such a reactor is disclosed in U.S. Pat. No. 5,942,197, the description of which is incorporated herein by reference. This preferred design is less susceptible to flooding than conventional countercurrent reactors because it incorporates passageways to bypass one or more catalyst beds. Bypass of at least a portion of the hydrogen treat gas is designed to occur when the pressure differential across the catalyst bed increases to a predefined threshold correlating to a near-flood condition. When gas bypasses the catalyst bed, the pressure differential across the catalyst bed decreases to permit the downward flow of liquid. When the pressure differential falls below a predefined level, the bypassing of gas is automatically stopped.

It is preferred that the feed streams be hydrotreated prior to ring opening to reduce sulfur content to low levels, preferably less than about 10 ppm, more preferably less than about 1 ppm, most preferably less than about 0.1 ppm. This is particularly desirable when high sulfur feeds are used in the ring opening process, since the ring opening catalysts are sensitive to high sulfur content.

Hydrotreating to reduce sulfur is referred to herein as hydrodesulfurization. Conventional hydrodesulfurization catalysts may be used to reduce the sulfur content of feed containing sulfur compounds to the preferred levels.

Non-limiting examples of conventional hydrodesulfurization catalysts which may be used to reduce the sulfur content of the feed include catalysts which comprise a Group VI metal with one or more Group VIII metals as promoters, the metals being on a refractory support. Conventional hydrodesulfurization processes are conducted at pressures ranging from about 50 to about 2000 psig, preferably from about 100 to about 1500 psig; liquid hourly space velocities ranging from about 0.2 to about 6 V/V/Hr, and a hydrogen gas rate of about 200 to about 5000 SCF/B.

Sulfur sorbents, including regenerable sulfur sorbents, may also be used to reduce the sulfur content of the feed. These materials are capable of removing the easy sulfur compounds, particularly hydrogen sulfide, under relatively mild sulfur removing conditions. Examples of sulfur sorbents include metal oxides. These systems are disclosed in U.S. Pat. Nos. 5,928,498; 5,925,239; 5,935,420; 4,003,823; U.S. Pat. No. 4,007,109; U.S. Pat. No. 4,087,348; U.S. Pat. No. 4,087,349; U.S. Pat. No. 4,119,528; and U.S. Pat. No. 4,127,470 all of which are incorporated by reference herein.

If significant aromatic compounds are present in the feed stream, it is desirable to saturate them. It is preferred that the feedstock contain less than about 20 wt. % total aromatic compounds, preferably less than about 15 wt. %, more preferably less than about 10 wt. %.

The aromatics saturation (ASAT) process may be performed in one or a series of reactors either before or after the ring opening process, since either mode will generally result in a product having increased cetane number due to the lowering of the aromatic content. Saturation of aromatics in the feed is preferred, however, prior to the ring opening process. This is because saturation of aromatics tends to result in the formation of additional naphthenes, providing additional material that can ultimately be converted using the catalyst of this invention to form compounds having a higher degree of linear paraffin functionality. In another preferred embodiment, a hydrodesulfurization reactor will be placed in front of (i.e., upstream) the aromatics saturation reactor so that the catalyst in the aromatics saturation reactor will contact low sulfur feedstock.

Any conventional aromatic saturation process may be used to hydrogenate the aromatic rings of the aromatic compounds in connection with this embodiment. Typical conditions for saturating aromatics-containing feedstocks include temperatures from about 150° C. to about 400° C., pressures from about 100 to about 2000 psig, space velocities from about 0.4 to about 6 V/V/Hr, and hydrogen gas rates from about 200 to 6000 standard cubic feet per barrel (SCF/B). Lower temperatures are found to be most desirable for the hydrogenation or saturation reactions since nonselective cracking reactions thereby are minimized. Selective saturation of the aromatics results in a saturated intermediate from the hydrogenation zone usually containing less than 15 weight % total aromatics.

Ring opening may also be practiced in a variety of stacked or mixed bed configurations along with aromatics saturation and sulfur removal. The stacked and mixed beds may occupy a single reactor or multiple reactors, and may take place in either co-current or countercurrent mode. The stacking of fixed beds of catalyst refers to the sequence of beds disposed with respect to the direction of flow of the liquid phase reactants. In a single reactor, such beds would be vertically disposed from top to bottom. In a series of reaction vessels the sequence is defined by the flow of the liquid phase.

A reactor may, for example, be loaded to have stacked layers of a sulfur reducing catalyst (e.g., a hydrodesulfurization (HDS) catalyst); a sulfur sorbent (sorbent); an aromatics saturation (ASAT) catalyst; and/or a ring opening (RO) catalyst. Specific examples of stacked catalyst arrangements include: HDS/ASAT/sorbent/RO; HDS/RO/ASAT; sorbent/ASAT/RO; and HDS/sorbent/ASAT/RO. Preferred mixed bed catalyst arrangements include: RO+ASAT; sorbent+RO; sorbent+ASAT+RO; and sorbent+HDS+RO. Conditions favoring the ring opening function are preferred.

The ring opened product of this invention may be recovered after the final processing step, i.e., after ring opening, after an optional ASAT final step, or after any further optional treatment step, according to conventional methods. The recovered product may be used directly, for example, as a diesel fuel, jet fuel, gas oil, and heating oil. It may also be blended with other petroleum products and used, for example, as a diesel fuel, jet fuel, gas oil, and heating oil. When blended, it is preferred that the ring opened product be blended with a petroleum stream having a boiling point ranging from about 175° C. to about 600° C., wherein the blend has a cetane number of at least about 40.

The Periodic Table of the Elements referred to herein appears on the inside cover page of the Merck Index, 12th Ed., Merck & Co., 1996.

This invention will be better understood with reference to the following examples, which are intended to illustrate specific embodiments within the overall scope of the invention as claimed.

General Experimental

In the examples, tertiary bond cleavage (%) is determined by dividing the wt. % yield of ring opened products involving tertiary centers by the total wt. % yield of all ring opened products and multiplying by 100. For example, methylcyclohexane ("MCH") tertiary bond cleavage in the examples= 100×(wt. % n-heptane/(wt. % n-heptane+wt. % isoheptanes)); for 1,2-dimethylcyclohexane ("1.2 DMCH") tertiary bond cleavage=100×((wt. % n-octane+wt. % 3-methylheptane)/(wt. % n-octane+wt. % 3-methylheptane+ wt. % 2,3-dimethylhexane+wt. % 3,4-dimethylhexane)). Metal loadings are in weight percent, based on the weight of the catalyst. For example, a catalyst of 0.9 wt. % Ir and 0.9 wt. % Pt, based on the weight of the catalyst is written as 0.9 Ir-0.9 Pt.

EXAMPLE 1

A 0.9 Ir catalyst was prepared by impregnating 50 g of reformer grade alumina extrudates with 28 ml of chloroiridic solution containing 16 mg of Ir/ml. The catalyst was dried at 120° C. for 24 hr and reduced at 450° C. for 3 hr. The catalyst was used to ring open methylcyclohexane under the following conditions: 300° C., 500 psig, 10 W/H/W, $H_2$/Oil 6. The results are shown in Table 1; products were identified by GC/MS.

EXAMPLES 2–4

The catalyst of Example 1 was used to ring open each of the three isomeric forms of dimethylcyclohexane, whose substitution pattern is more representative of that found in distillate range streams, under the following conditions: 325° C., 500 psig, 10 W/H/W, $H_2$/Oil=6. The results are shown in Table 1.

EXAMPLE 5

The catalyst of Example 1 was used to ring open 1,2,4-trimethylcyclohexane ("1,2,4-TMCH"), whose substitution pattern is highly representative of that found in distillate range streams, under the following conditions: 325° C., 500 psig, 2 W/H/W, $H_2$/Oil=6. The results are shown in Table 1.

TABLE 1

| Example | Feed | Conversion, Wt. % | Tertiary Bond Cleavage, % |
|---|---|---|---|
| 1 | MCH | 61 | 5 |
| 2 | 1,2-DMCH | 55 | 18 |
| 3 | 1,3-DMCH | 49 | 24 |
| 4 | 1,4-DMCH | 50 | 18 |
| 5 | 1,2,4-TMCH | 44 | 56 |

The data in Table 1 indicate that at about the same general range of conversion the degree of tertiary bond cleavage over Ir increases from about 5% of the total to about 50%. The trend coincides with the number of tertiary centers in the feed.

EXAMPLE 6

The procedure of Example 1 was used to prepare a 0.01Pt-0.9Ir catalyst by implementing reformer grade alumina extrudates with stock solutions of chloroiridic and chloroplatinic acids (28 mg Pt/ml). The catalyst was dried and reduces as in Example 1. The 0.01Pt-0.9Ir catalyst was used to ring open 1,2-dimethylcyclohexane, and the results appear in Table 2.

EXAMPLE 7

The procedure of Example 1 was used to prepare a 0.05Pt-0.9Ir catalyst by implementing reformer grade alumina extrudates with stock solutions of chloroiridic and chloroplatinic acids. The catalyst was dried and reduced as in Example 1. The 0.05Pt-0.9Ir catalyst was used to ring open 1,2-dimethylcyclohexane, and the results are shown in Table 2.

EXAMPLE 8

The procedure of Example 1 was used to prepare a 0.1Pt-0.9Ir catalyst by impregnating reformer grade alumina extrudates with stock solutions of chloroiridic and chloroplatinic acids (28 mg Pt/ml). The catalyst was dried and reduced as in Example 1. The 0.1Pt-0.9Ir catalyst was used to ring open 1,2-dimethylcyclohexane, and the results appear in Table 2.

EXAMPLE 9

The procedure of Example 1 was used to prepare a 0.6Pt-0.9Ir catalyst by impregnating reformer grade alumina extrudates with stock solutions of chloroiridic and chloroplatinic acids (28 mg Pt/ml). The catalyst was dried and reduced as in Example 1. The 0.6Pt-0.9Ir catalyst was used to ring open 1,2-dimethylcyclohexane, and the results are shown in Table 2.

EXAMPLE 10

The procedure of Example 1 was used to prepare a 0.9Pt-0.9Ir catalyst by impregnating reformer grade alumina extrudates with stock solutions of chloroiridic and chloroplatinic acids (28 mg Pt/ml). The catalyst was dried and reduced as in Example 1. The 0.9Pt-0.9Ir catalyst was used to ring open 1,2-dimethylcyclohexane, and the results appear in Table 2.

EXAMPLE 11

The procedure of Example 1 was used to prepare a 1.3Pt-0.9Ir catalyst by impregnating reformer grade alumina extrudates with stock solutions of chloroiridic and chloroplatinic acids (28 mg Pt/ml). The catalyst was dried and reduced as in Example 1. The 1.3Pt-0.9Ir catalyst was used to ring open 1,2-dimethylcyclohexane, and the results appear in Table 2.

TABLE 2

| (300° C.; 500 psig; 10 W/H/W; $H_2$/Oil = 6) | | | | |
|---|---|---|---|---|
| Example | Catalyst | Conversion, Wt. % | Ring Opening Yield, Wt. % | Tertiary Bond Cleavage, % |
| 2 | 0.9 Ir | 30 | 20 | 18 |
| 6 | 0.01 Pt—0.9 Ir | 48 | 34 | 35 |
| 7 | 0.05 Pt—0.9 Ir | 47 | 33 | 33 |
| 8 | 0.1 Pt—0.9 Ir | 33 | 24 | 29 |
| 9 | 0.6 Pt—0.9 Ir | 32 | 16 | 27 |
| 10 | 0.9 Pt—0.9 Ir | 14 | 10 | 30 |
| 11 | 1.3 Pt—0.9 Ir | 10 | 7 | 31 |

The data reveal a substantial increase in the degree of tertiary bond cleavage for the Pt—Ir catalysts of this invention over the Ir only catalyst of Example 1. The degree of improvement for reaction at the tertiary center ranges from about 50% to about 95% and is independent of catalyst composition over the range 0.01Pt-1.3Pt. There is a decrease in activity with increasing Pt loading, which can be compensated by increasing reaction temperature. The increase in both activity and tertiary bond selectivity at the low Pt loadings of Examples 6,7, and 8 highlights the added value of these bimetallic catalysts.

EXAMPLE 12

A 0.1Rh-0.9Ir catalyst was prepared as described in Example 8 by substituting a Rh stock solution for Pt. The catalyst was used to ring open 1,2-dimethylcyclohexane. The conversion and tertiary bond cleavage are shown in Table 3 and compared to that of Examples 2 and 8. The 0.1 Rh-0.9 Ir catalyst shows a substantial increase in the degree of tertiary bond cleavage vs. the 0.9 Ir catalyst.

TABLE 3

| Example | Conversion, Wt. % | Tertiary Bond Cleavage, % |
|---|---|---|
| 2 | 55 | 18 |
| 8 | 33 | 29 |
| 12 | 37 | 33 |

EXAMPLE 13

A 0.9Pd-0.9Ir catalyst was prepared as described in Example 10 except a Pd stock solution was substituted for the Pt solution. The catalyst was activated as described and tested in the ring opening of 1,2-dimethylcyclohexane. The 0.9Pd-0.9Ir catalyst has a conversion of 4%, and the selectivity for tertiary bond cleavage was equal to the of 0.9Ir only, 18%. This Pd—Ir catalyst offers no tertiary bond cleavage credit over Ir only. All Ir-Group VIII catalysts are therefore not equally effective for selective ring opening.

EXAMPLE 14

The procedure of Example 5 was repeated where 1,2,4-trimethylcyclohexane was subjected to ring opening over a 0.9Pt-0.9Ir catalyst. The results are shown in Table 4. This example illustrates that catalysts of this invention have improved propensity for teriary bond cleavage over prior art catalysts even with highly substituted rings.

TABLE 4

| Example | Conversion, Wt. % | Tertiary Bond Cleavage, % |
|---|---|---|
| 5 | 44 | 56 |
| 14 | 56 | 75 |

EXAMPLE 15

The procedure of Example 3 was repeated using a 0.1Pt-0.9Ir catalyst. The results are summarized in Table 5.

TABLE 5

| Example | Conversion, Wt. % | Tertiary Bond Cleavage, % |
|---|---|---|
| 3 | 49 | 24 |
| 15 | 72 | 36 |

EXAMPLE 16

The catalyst of Example 1 was used to ring open 1,2,4-trimethylcyclohexane at 300° C., 500 psig, 1 LHSV, 5000 SCF/B hydrogen. The results are summarized in Table 6.

EXAMPLES 17–20

The catalysts of Examples 8–11 were used to ring open 1,2,4-trimethylcyclohexane at the conditions of Example 16. The results appear in Table 6.

TABLE 6

(300° C.; 500 psig; 1 W/H/W; $H_2$/Oil + 6)

| Example | Catalyst | Conversion, Wt. % | Ring Opening Yield, Wt. % | Tertiary Bond Cleavage, % |
|---|---|---|---|---|
| 16 | 0.9Ir | 39 | 22 | 40 |
| 17 | 0.1Pt—0.9Ir | 61 | 34 | 77 |
| 18 | 0.6Pt—0.9Ir | 39 | 23 | 77 |
| 19 | 0.9Pt—0.9Ir | 56 | 28 | 75 |
| 20 | 1.3Pt—0.9Ir | 46 | 22 | 78 |

The data illustrate that the bimetallic catalysts of this invention have a substantially higher preference for tertiary bond cleavage than the Ir only catalyst leading to a product rich in mono- and dibranched nonanes and lean in tribranched $C_9$ paraffins.

Preparation of Saturated Cyclic Feedstock A

An aromatics solvent stream containing primarily $C_{11}$ and $C_{12}$ naphthalenes with an API gravity of 10 was hydrogenated over 180 g (250 cc) of a 0.6 wt. % Pt on alumina catalyst. The catalyst was prereduced in flowing hydrogen at 750° F. for 16 hr at atmospheric pressure. The aromatics solvent feedstock was passed over the catalyst at 1800 psig, 550° F., 1 LHSV, 7000 SCF/B hydrogen treat gas rate. The saturated product had an API gravity of 31.6 and contained less than 0.1 wt. % aromatics and greater than 99 wt. % naphthenes.

EXAMPLE 21

A reactor was charged with the 0.9 wt. % Ir catalyst of Example 1. Saturated cyclic feedstock A was processed over the Ir catalyst at 600° F., 650 psig, 3000 SCF/B $H_2$, 0.5 LHSV. Key results from this run are summarized in Table 7.

EXAMPLE 22

A reactor was charged with the 0.05 wt. % Pt-0.9 wt. % Ir catalyst of Example 7. Saturated cyclic feedstock A was processed over the Pt—Ir catalyst at 600° F., 650 psig, 3000 SCF/B $H_2$, 0.5 LHSV. Key results from this run are summarized in Table 7.

TABLE 7

Ring Opening Of Saturated Cyclic Feedstock A Over 0.9Ir and 0.05Pt—0.9Ir Catalysts

| Catalyst | Feed | 0.9Ir | 0.05Pt—0.9Ir |
|---|---|---|---|
| $C_6^-$ Gas, wt. % | — | 0.7 | 2.8 |
| Total Liquid Product, wt. % | 100 | 97.2 | 95.2 |
| 375° F.$^+$ Yield, wt. % | 89.0 | 85.3 | 82.0 |
| Total Liquid Product API | 31.6 | 33.7 | 35.9 |
| Paraffins, wt. % | 0.9 | 1.5 | 4.1 |
| One Ring Naphthenes, wt. % | 18.3 | 25.6 | 39.4 |
| Two Ring Naphthenes, wt. % | 80.9 | 72.9 | 56.5 |
| Ring Disappearance, mol. % | — | 6.6 | 21.8 |

The wt. % yield of total liquid product and of 375° F.$^+$ distillate is lower over the catalyst of this invention due to incrementally higher gas make. However, the volumetric yield of the Pt—Ir catalyst is favored by the higher product API. More significantly, the greater degree of ring disappearance over the Pt—Ir catalyst at comparable conversion as measured by distillate yield demonstrates higher activity for the Pt—Ir catalyst relative to Ir only.

Having now fully described this invention, it will be appreciated by those skilled in the art that the invention can be performed within a wide range of parameters within what is claimed, without departing from the spirit and scope of the invention.

What is claimed is:

1. A naphthene ring opening catalyst comprising about 0.1 wt. % to about 2 wt. % Ir in combination with Pt in an amount in the range of about 0.01 wt. % to about 1.3 wt. %, wherein the concentration of Ir is always greater than the concentration of Pt, which is effective for opening a naphthene ring-containing compound at a tertiary carbon site, wherein said naphthene ring opening catalyst is supported on alumina.

2. The naphthene ring opening catalyst of claim 1 wherein the catalyst is capable, when contacted with an amount of 1-2dimethylcyclohexane under catalytic ring opening conditions, of ring opening at least about 20% of the amount of 1,2-dimethylcyclohexane at the tertiary carbon site.

3. The catalyst of claim 2 wherein the catalytic ring opening conditions include a temperature ranging from about 150° C. to about 400° C., a total pressure ranging from about 100 to about 3,000 psig, a liquid hourly space velocity ranging from about 0.1 to about 10 V/V/Hr, and a hydrogen treat gas rate ranging from about 200 to about 10,000 SCF/B.

4. The naphthene ring opening catalyst of claim 3 wherein the catalyst is capable of ring opening at least about 30% of the amount of 1,2-dimethylcyclohexane at the tertiary carbon site.

5. The naphthene ring opening catalyst of claim 4 wherein the catalyst is capable of ring opening between about 30% and about 40% of the amount of 1,2-dimethylcyclohexane at the tertiary carbon site.

6. A process for opening naphthene rings of naphthene ring-containing compounds in a feed stream, comprising:

providing a naphthene ring-containing feed stream; and contacting the naphthene ring-containing feed stream with a catalyst comprising about 0.1 wt. % to about 2 wt. % Ir in combination with Pt in an amount in the range of about 0.01 wt. % to about 1.3 wt. %, wherein the concentration of Ir is always greater than the concentration of Pt, which is effective for opening a naphthene ring-containing compound at a tertiary carbon site under effective ring opening conditions wherein said catalyst is supported on alumina.

7. The process of claim 6 further comprising ring opening at the tertiary carbon site, thereby forming a ring opened product having increased linear paraffin functionality relative to that of the feed stream.

8. The process of claim 7, further comprising recovering the ring opened product.

9. The process of claim 8 further comprising blending the ring opened product with a petroleum stream having a boiling point of about 175° C. to about 600° C., wherein the blend has a cetane number of at least about 40.

10. The process of claim 6 wherein ring opening is carried out at a temperature of from about 150° C. to about 400° C., a total pressure from about 100 to about 3,000 psig, a liquid hourly space velocity of about 0.1 to about 10 V/V/Hr, a hydrogen treat gas rate of about 200 to about 10,000 standard cubic feet per barrel (SCF/B), and wherein the feed stream is a petroleum feed stream which has a boiling point ranging from about 175° C. to about 600° C.

11. The process of claim 10 wherein the petroleum feed stream is at least one of diesel fuel, jet fuel, heating oil, vacuum gas oil, and light cycle oil.

12. The process of claim 6 wherein the naphthene ring-containing feed stream has a sulfur content of less than about 10 ppm and contains less than about 20 wt. % total aromatic compounds.

13. The process of claim 6 wherein the catalyst is capable, when contacted with an amount of 1,2-dimethylcyclohexane under catalytic ring opening conditions, of ring opening at least about 20% of the amount of 1,2-dimethylcyclohexane at the tertiary carbon site.

14. The process of claim 13 wherein the catalytic ring opening conditions include a temperature ranging from about 150° C. to about 400° C., a total pressure ranging from about 100 to about 3,000 psig, a liquid hourly space velocity ranging from about 0.1 to about 10 V/V/Hr, and a hydrogen treat gas rate ranging from about 200 to about 10,000 SCF/B.

15. The process of claim 14 wherein the catalyst is capable of ring opening at least about 30% of the amount of 1,2-dimethylcyclohexane at the tertiary carbon site.

16. The process of claim 14 wherein the catalyst is capable of ring opening between about 30% and about 40% of the amount of 1,2-dimethylcyclohexane at the tertiary carbon site.

* * * * *